(12) United States Patent
Takata

(10) Patent No.: US 8,201,437 B2
(45) Date of Patent: Jun. 19, 2012

(54) ALCOHOL DETECTION SYSTEM AND METHOD FOR VEHICLE

(75) Inventor: Takashi Takata, Nagoya (JP)

(73) Assignee: Denso Corporation, Kariya (JP)

( * ) Notice: Subject to any disclaimer, the term of this patent is extended or adjusted under 35 U.S.C. 154(b) by 533 days.

(21) Appl. No.: 12/538,325

(22) Filed: Aug. 10, 2009

(65) Prior Publication Data

US 2010/0043524 A1     Feb. 25, 2010

(30) Foreign Application Priority Data

Aug. 19, 2008    (JP) ................. 2008-211001

(51) Int. Cl.
    *G01N 33/497*     (2006.01)
    *G01N 1/22*     (2006.01)
    *B60K 28/06*     (2006.01)

(52) U.S. Cl. ........................... 73/23.3; 180/272

(58) Field of Classification Search .................. 73/23.2; 180/272; 702/183

See application file for complete search history.

(56) References Cited

U.S. PATENT DOCUMENTS

| | | | | |
|---|---|---|---|---|
| 3,903,726 A | * | 9/1975 | Hirosawa et al. | 73/23.3 |
| 4,093,945 A | * | 6/1978 | Collier et al. | 180/272 |
| 4,738,333 A | * | 4/1988 | Collier et al. | 180/272 |
| 4,809,810 A | * | 3/1989 | Elfman et al. | 180/272 |
| 5,531,225 A | * | 7/1996 | Nawata et al. | 600/532 |
| 6,748,792 B1 | * | 6/2004 | Freund et al. | 73/23.3 |
| 6,853,956 B2 | * | 2/2005 | Ballard et al. | 702/183 |
| 6,967,581 B2 | * | 11/2005 | Karsten | 340/576 |
| 7,218,236 B2 | * | 5/2007 | Mobley et al. | 340/576 |
| 7,481,292 B2 | * | 1/2009 | Mobley et al. | 180/272 |
| 2006/0237252 A1 | * | 10/2006 | Mobley et al. | 180/272 |
| 2006/0237253 A1 | * | 10/2006 | Mobley et al. | 180/272 |
| 2006/0237254 A1 | * | 10/2006 | Mobley et al. | 180/272 |
| 2006/0238362 A1 | * | 10/2006 | Mobley et al. | 340/576 |
| 2006/0239856 A1 | * | 10/2006 | Mobley et al. | 422/84 |
| 2008/0048846 A1 | | 2/2008 | Nagai et al. | |
| 2008/0250829 A1 | * | 10/2008 | Kamiki | 70/344 |
| 2010/0025585 A1 | * | 2/2010 | Taguchi et al. | 250/339.13 |
| 2010/0188232 A1 | * | 7/2010 | Lambert et al. | 340/573.1 |
| 2011/0050407 A1 | * | 3/2011 | Schoenfeld et al. | 340/426.11 |

FOREIGN PATENT DOCUMENTS

JP       5-34203       2/1993

(Continued)

OTHER PUBLICATIONS

Japanese Office Action dated Apr. 8, 2010, issued in corresponding Japanese Application No. 2008-211001, with English translation.

*Primary Examiner* — Lisa Caputo
*Assistant Examiner* — Punam Roy
(74) *Attorney, Agent, or Firm* — Nixon & Vanderhye PC

(57) ABSTRACT

An alcohol detection system for a vehicle has an alcohol sensor, for which alcohol measurement preparation processing such as heating the alcohol sensor to a predetermined temperature is performed, so that the alcohol sensor operates under the stable operation state. The alcohol measurement preparation processing is started, before a driver actually gets in the vehicle. For example, the preparation processing is started, when a predetermined manipulation of a driver on the vehicle before entering the vehicle is detected. The manipulation may be unlocking or opening of a vehicle door.

20 Claims, 13 Drawing Sheets

FOREIGN PATENT DOCUMENTS

| | | |
|---|---|---|
| JP | 05-034203 | 2/1993 |
| JP | 50-34203 | 2/1993 |
| JP | 6-4977 | 1/1994 |
| JP | 06-004977 | 1/1994 |
| JP | 60-04977 | 1/1994 |
| JP | 07-287179 | 10/1995 |
| JP | 7-287179 | 10/1995 |
| JP | 08-150853 | 6/1996 |
| JP | 09-243627 | 9/1997 |
| JP | 9-243627 | 9/1997 |
| JP | 2005-118177 | 5/2005 |
| JP | 2005-171886 | 6/2005 |
| JP | 2005-224319 | 8/2005 |
| JP | 2008-045374 | 2/2008 |
| JP | 2008-137624 | 6/2008 |
| JP | 2008-183927 | 8/2008 |

* cited by examiner

US 8,201,437 B2

ALCOHOL DETECTION SYSTEM AND METHOD FOR VEHICLE

CROSS REFERENCE TO RELATED APPLICATION

This application is based on and incorporates herein by reference Japanese Patent Application No. 2008-211001 filed on Aug. 19, 2008.

FIELD OF THE INVENTION

The present invention relates to an alcohol detection system and method for a vehicle.

BACKGROUND OF THE INVENTION

Drunk driving of a vehicle (for example, automobile) is now a serious social problem. A driver is therefore strictly prohibited from driving a vehicle under the influence of alcohol drinking. However it all depends on a driver whether he or she refrains from driving a vehicle after drinking alcohol. JP 2005-224319A proposes technology, which forcibly restrains a driver under the influence of alcohol drinking from driving a vehicle. According to this technology, an alcohol detection device (alcohol concentration measurement device) is provided in a vehicle so that an engine start operation is prohibited, for example, unless the alcohol detection device confirms that the driver is free from the influence of alcohol drinking.

The alcohol detection device normally has an alcohol sensor, which measures concentration of alcohol contained in a breath air of the driver, to determine degree of the influence of alcohol drinking.

According to the conventional alcohol detection device, a preparatory operation is performed for a wait period of several tens of seconds before the actual measurement of alcohol to improve the accuracy in measurement of the alcohol sensor. This wait period will necessarily irritate the driver, particularly drivers who have not drunk any alcohol.

SUMMARY OF THE INVENTION

It is therefore an object of the present invention to provide an alcohol detection system and method, which can start measurement of alcohol concentration in a breath of a driver with only a short wait period.

According to one aspect of the present invention, an alcohol detection system detects alcohol concentration in breath air of a driver seating in a vehicle, permits normal travel of the vehicle when alcohol concentration measured under the predetermined stable operation state is below a threshold level, and prohibits travel of the vehicle over a predetermined travel speed when the alcohol concentration is over the threshold level. The alcohol detection system detects a pre-driving output signal outputted necessarily before an engine switch is manipulated, and instruct start of an alcohol measurement preparation operation when the pre-driving output signal is detected. Thus, measurement of alcohol concentration can be started without necessitating long wait time.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

The present invention will be described in detail with reference to an embodiment and its modifications.

Figure 1:
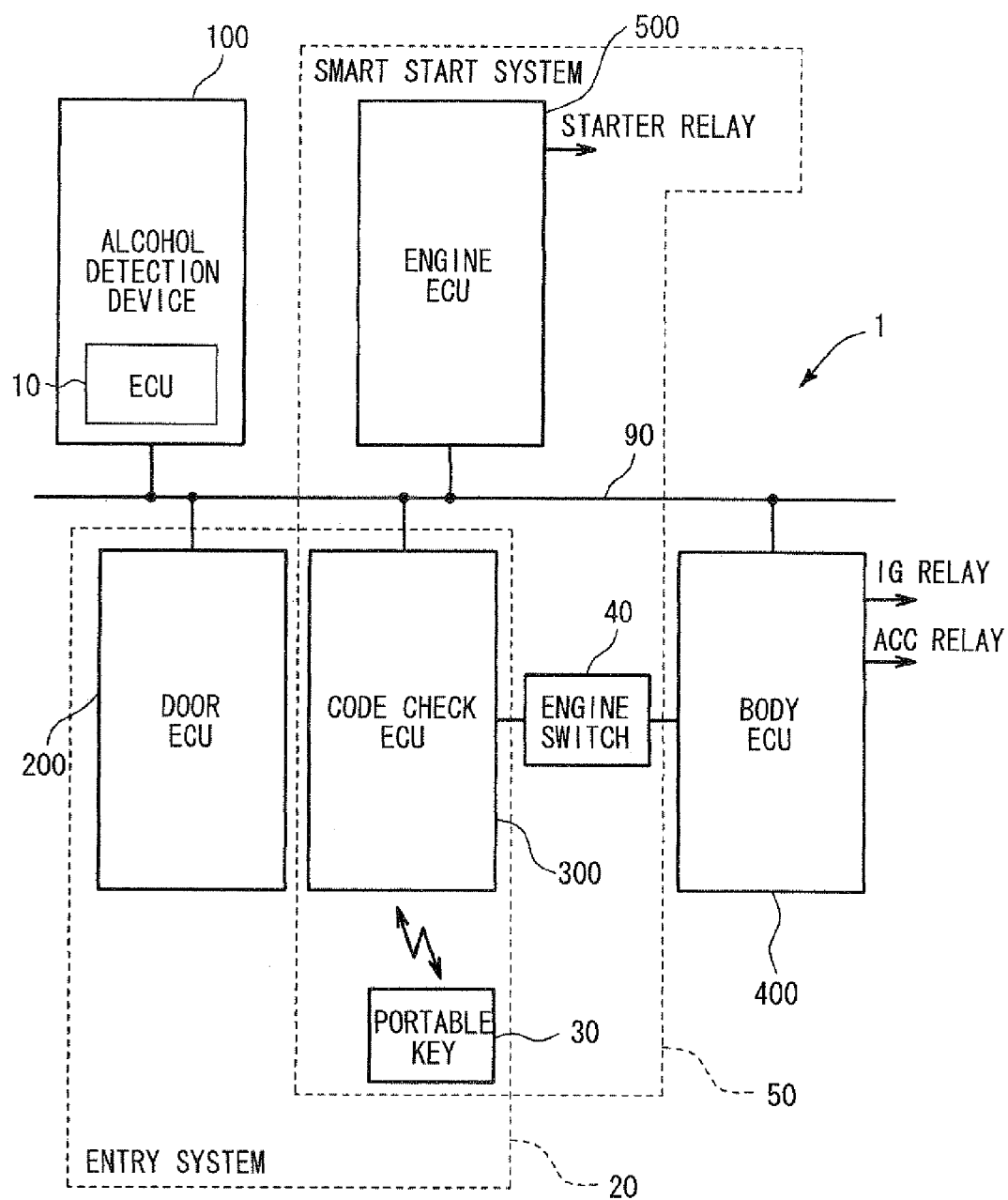
FIG. 1 is a block diagram of an alcohol detection system for a vehicle according to an embodiment of the present invention.

Referring first to FIG. 1, an alcohol detection system 1 for a vehicle is configured with an alcohol detection device 100 including an alcohol detection ECU 10, a smart entry system (keyless entry system) 20 including a door ECU 200 and a code check ECU 300, a body ECU 400, and an engine ECU 500, all of which are connected to one another through an in-vehicle local area network (LAN) 90 to cooperate one another. Each of the ECUs 10, 200, 300, 400 and 500 is configured as a microcomputer including a CPU, a ROM, a RAM and the like.

Figure 8:
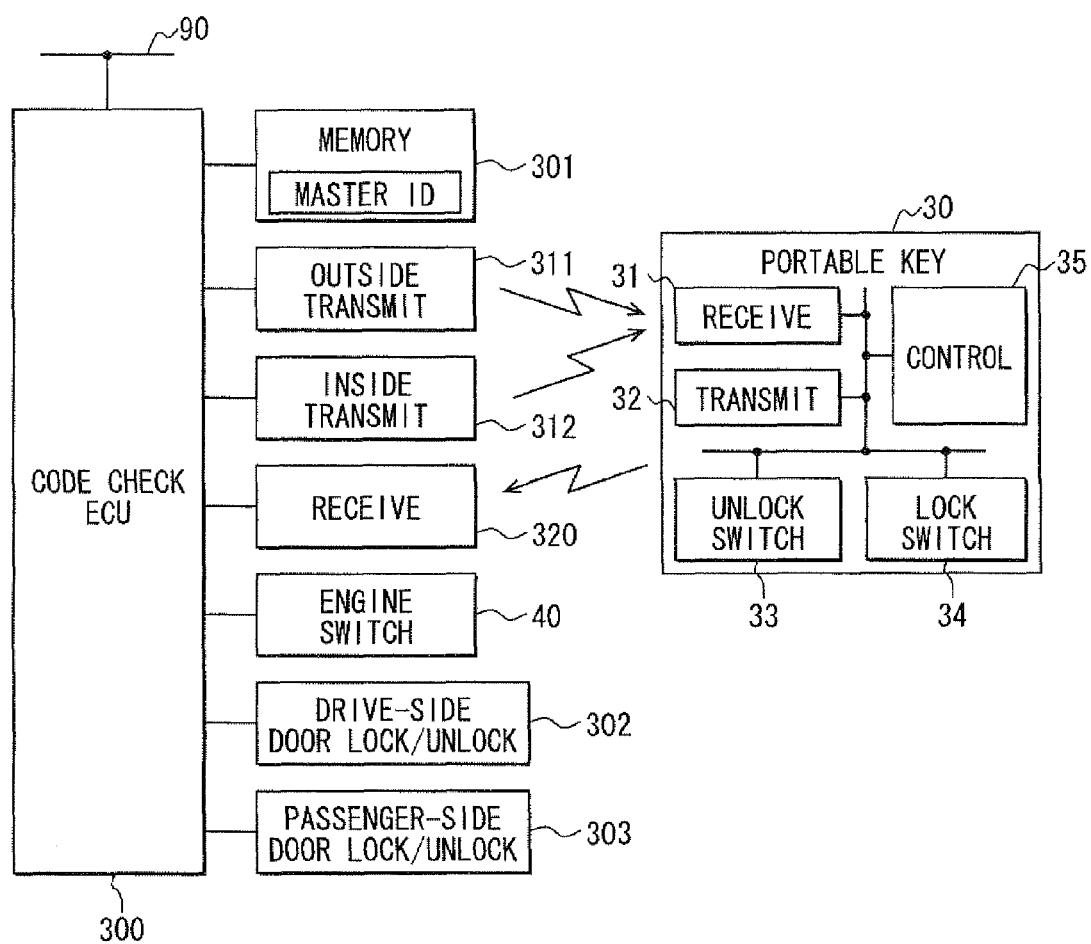
FIG. 8 is a block diagram of a part of a smart entry system.
Figure 9:
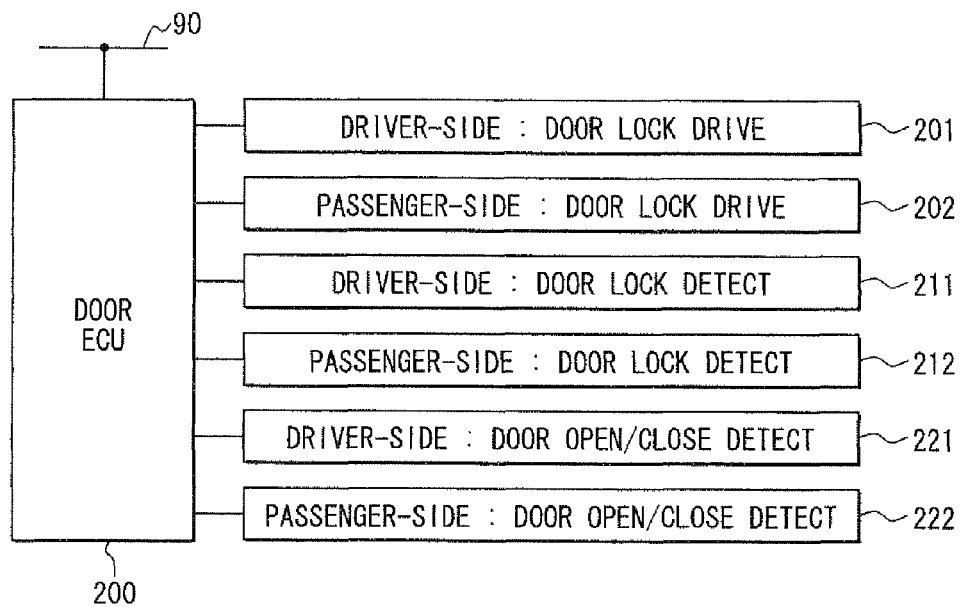
FIG. 9 is a block diagram of the other part of the smart entry system.

As shown in FIGS. 8 and 9, the smart entry system 20 is configured with a portable key 30, which is a mobile device (smart key in the smart entry system) for radio communications, the code check ECU 300 for checking a key, and the door ECU 200 for controlling locking and unlocking doors (specifically, door lock mechanisms).

Figure 10:
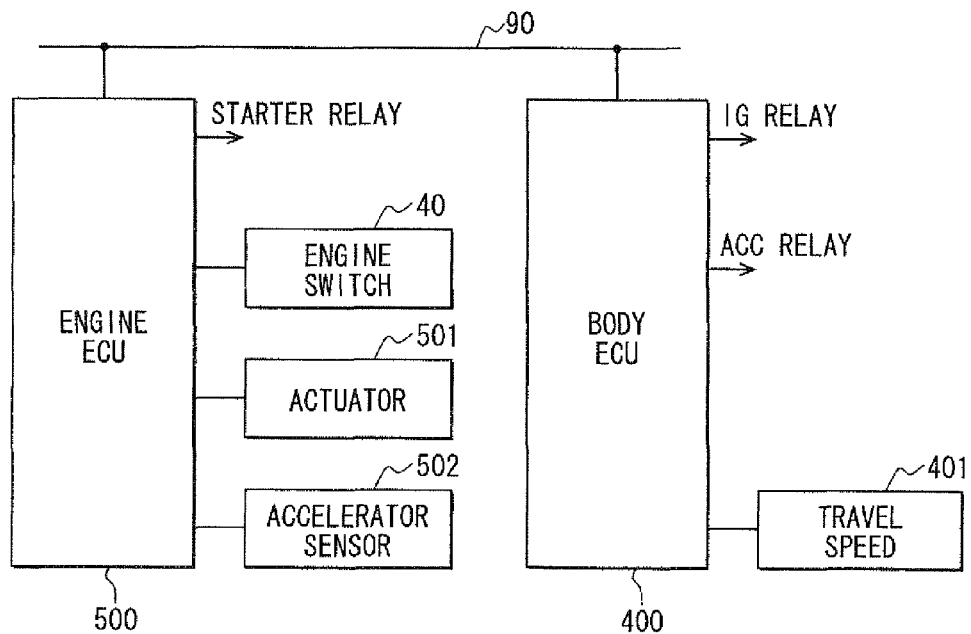
FIG. 10 is a block diagram of a part of the alcohol detection system.

As shown in FIG. 10, the body ECU 400 is configured to produce outputs for turning on an accessory (ACC) relay and an ignition (IG) relay based on manipulation on an engine switch 40. The engine ECU 500 is configured to produce an output for turning on a starter relay based on predetermined engine start manipulation on the engine switch 40, and perform conventional engine drive control (fuel injection control and the like) by driving an actuator 501 based on detection results of an accelerator sensor 502 and other engine system sensors.

Figure 2A:
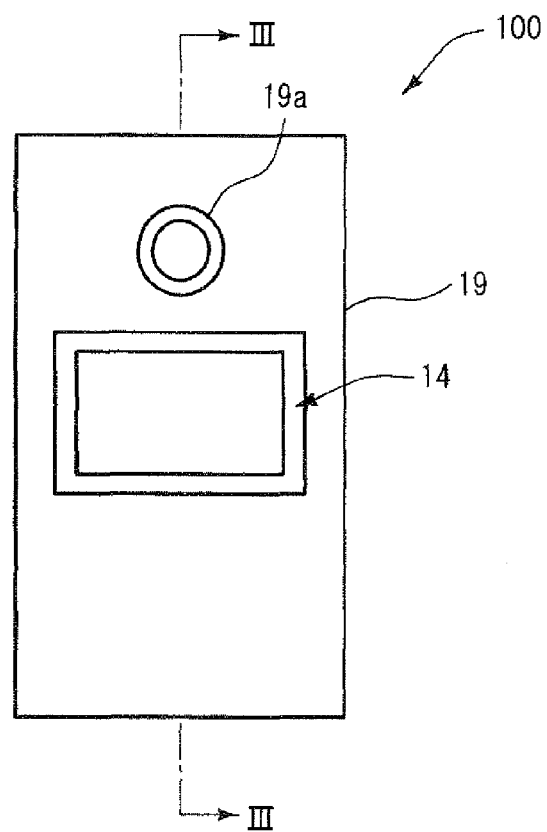
FIGS. 2A and 2B are a front view and a rear view of an alcohol detection device, respectively.
Figure 2B:
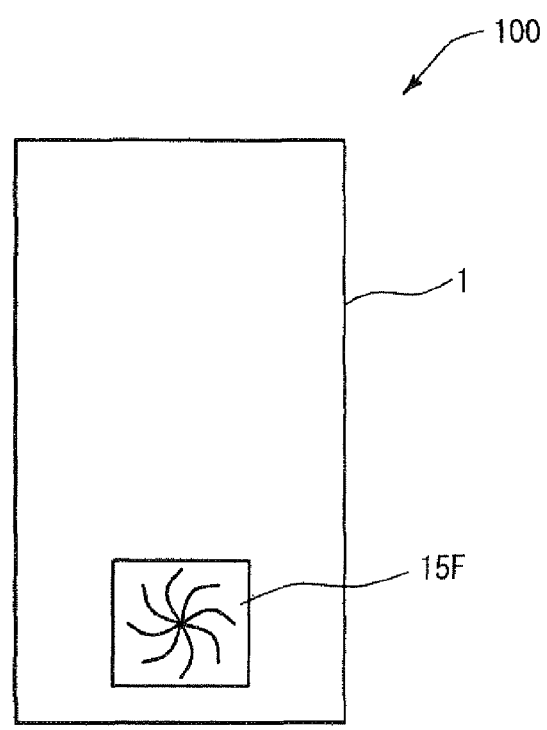

The alcohol detection device 100 is configured as shown in FIGS. 2A and 2B. The alcohol detection device 100 has a breath inlet 19a and a display unit 14. The breath inlet 19a is provided at a front upper part of a casing 19 for taking in breath air blown by a driver (user of a vehicle) to be tested. The display unit 14 is provided as an indicator at a lower part of the breath inlet 10a for displaying measured concentration of alcohol contained in the breath supplied through the breath inlet 19a. The breath inlet 10a is tubular and extends from the front surface of the casing 19. The alcohol detection device 100 also has an exhaust fan 15F, which is provided at a lower part on a rear surface of the casing 19 for forcibly exhausting the breath air subjected to the measurement of alcohol concentration.

Figure 3:
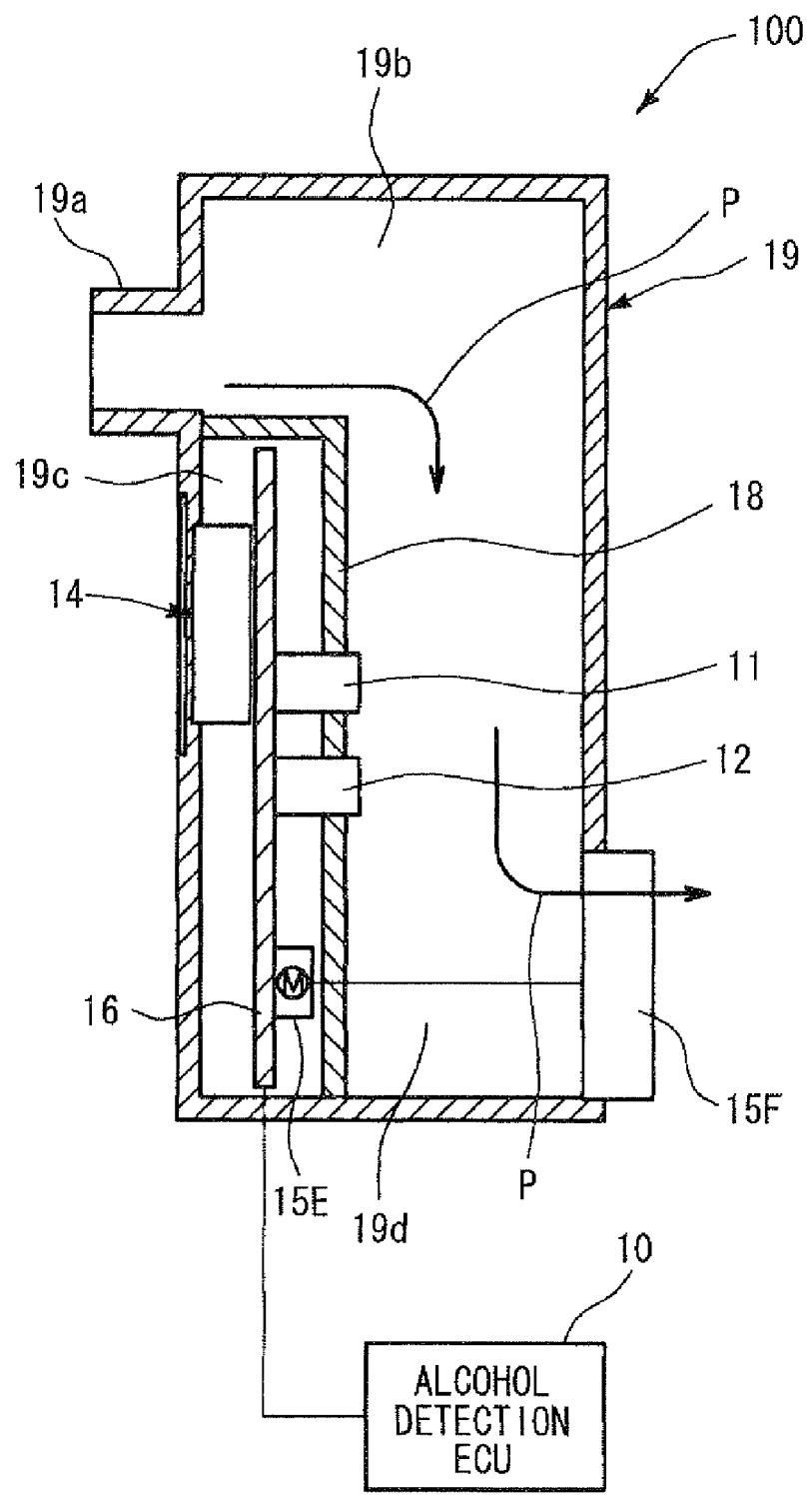
FIG. 3 is a cross sectional view of the alcohol detection device taken along a line III-III in FIG. A.

The display unit 14 is a LED display unit, for example. As shown in FIG. 3 in detail, the display unit 14 for displaying the measured concentration of the alcohol is mounted on a substrate 16 and attached to the front part of the casing 19 so that the displayed concentration of the alcohol may be visible from an outside of the front part of the casing 19. The display unit 14 may alternatively be an indicator unit or a meter display unit, which are provided on an upper part of a center console of the vehicle.

An alcohol sensor 11 and a residual gas sensor (detection part) 12 are attached to a rear part of the substrate 16. The substrate 16 is enclosed within a cover 18 provided in the casing 19. The cover 18 partitions the inside space of the casing 19 into a breath air measurement chamber 19b and a substrate accommodating chamber 19c, which accommodates the substrate 16. Top parts of the alcohol sensor 11 and the residual gas sensor 12 protrude from the cover 18 into the measurement chamber 19b. The volume of the measurement chamber 19b is determined to correspond to volume or air, which an adult person normally breathes. The alcohol sensor and the measurement chamber 19 form an alcohol detection part.

The alcohol sensor 11 of the alcohol detection device 100 requires alcohol measurement preparation processing (operation) to change from an initial state to a stable operation state in starting the measurement of alcohol concentration.

Figure 4:
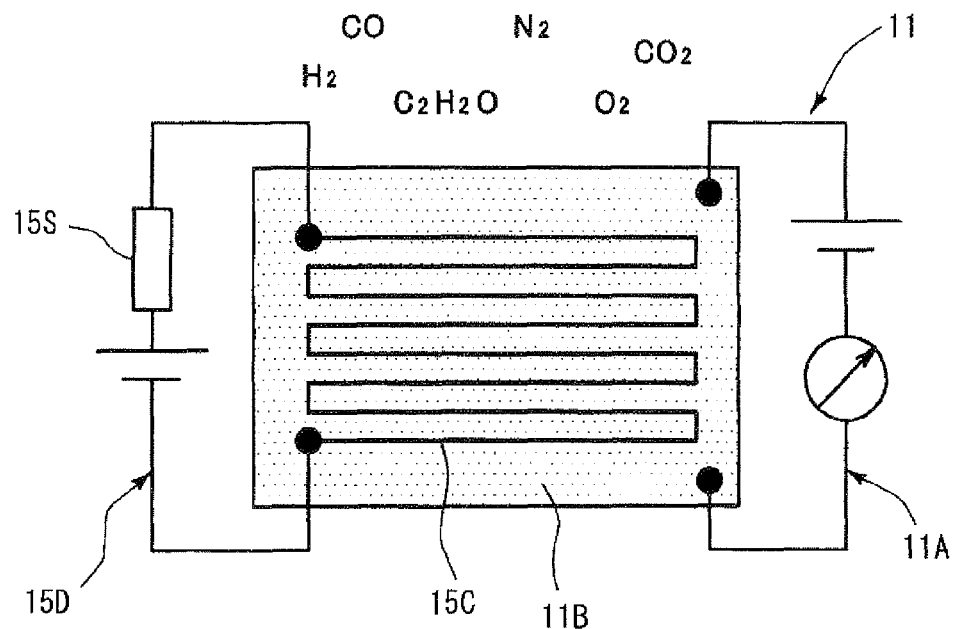
FIG. 4 is a schematic view of an alcohol sensor.

As shown in FIG. 4, the alcohol sensor 11 is a semiconductor sensor in which a coil 15C made of platinum is coated with a metal oxide 11B such as a tin oxide and sintered. In clean air, which contains no alcohol, oxygen atoms in the air and electrons of the metal oxide (tin oxide) 11B are coupled, and hence the metal oxide 11B does not allow flow of electric current. Under this state, a current is supplied to the coil 15C to heat the metal oxide 11B to predetermined temperature (aging). If the breath air containing alcohol contacts the metal oxide 11B after the heating, the alcohol in the breath air and oxygen atoms react each other. As a result, the oxygen atoms coupled with the electrons of the metal oxide 11B are decoupled and deprived. Electrons in the metal oxide 11B are freed to allow the flow of current. A detection circuit 11A detects this change (current) and measures a change in the electric resistance of the metal oxide 11B as a measurement of the alcohol concentration in the breath air.

The residual gas sensor 12 is provided to detect the residual gas remaining in the measurement chamber 19b thereby measuring the internal state of the breath air measuring chamber 19b. The residual gas sensor may be an oxygen sensor, which measures oxygen concentration in the measurement chamber 19b. By checking whether the breath air in the measurement chamber 19b has been exhausted or purged out, it is checked whether new measurement can be performed. It is also possible to attach a carbon dioxide sensor in addition to the oxygen sensor, so that the carbon dioxide concentration in the measurement chamber 19b may be measured.

Figure 5:
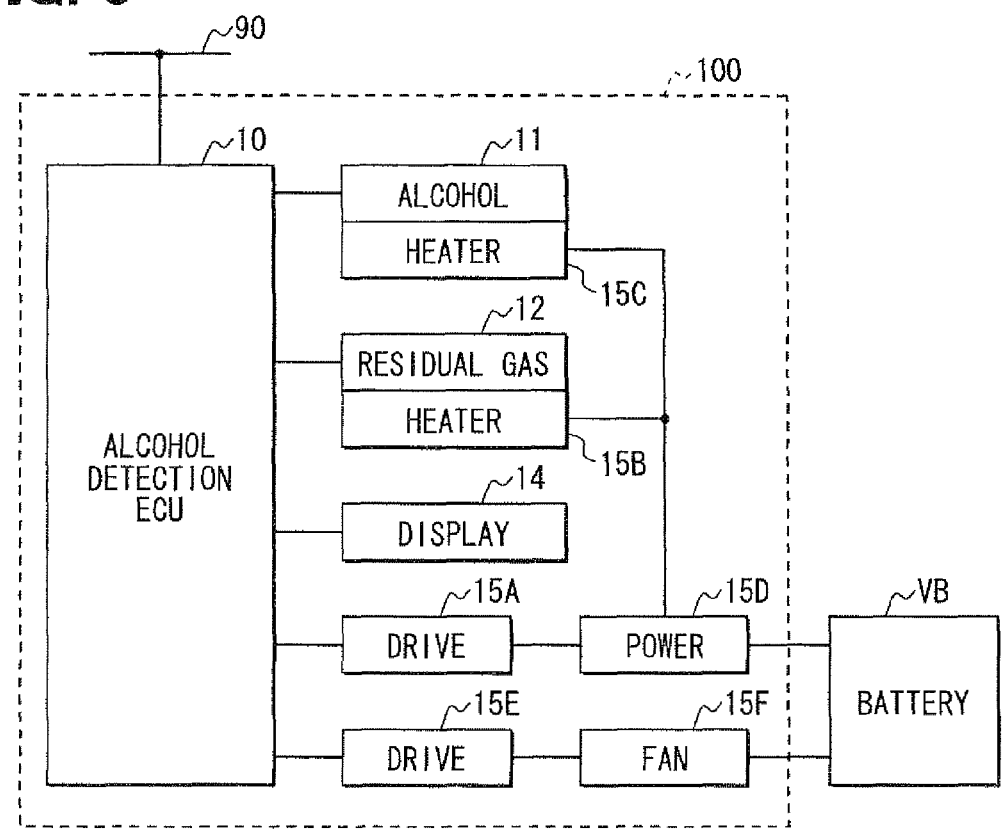
FIG. 5 is a block diagram of the alcohol detection device.

In the alcohol detection device 100, as shown in FIG. 5, the alcohol sensor 11, the residual gas sensor 12 and the display unit 14 are connected to the alcohol detection ECU 10. The alcohol concentration is measured by the alcohol sensor 11 by manipulating a measurement start switch (not shown). The alcohol detection ECU 10 calculates the alcohol concentration based on the detection result information of the alcohol sensor 11, and the calculation result is displayed by the display unit 14.

The alcohol detection ECU 10 is connected to a manipulation part (measurement preparation manipulation part) for implementing the measurement preparation processing. The measurement preparation manipulation part is configured with the exhaust fan 15F and the coil (heater) 15C. A vehicle storage battery VB is provided as a power source for the alcohol detection device 100. The exhaust fan 15F is configured to be driven by a motor, which is energized with the electric power of the vehicle battery VB, and connected to the alcohol detection ECU 10 to be controlled through a drive circuit 1SE. The temperature inside the measurement chamber 19b is preferably detected by a temperature sensor (not shown) so that the alcohol detection ECU 10 controls the rotation speed of the exhaust fan 15F based on the detected temperature in the measurement chamber 19b. The heater 15C generates heat, when energized by the vehicle battery VB through a power circuit 15D. The alcohol detection ECU 10 controls the power circuit 15D through a drive circuit 15A.

Figure 7:
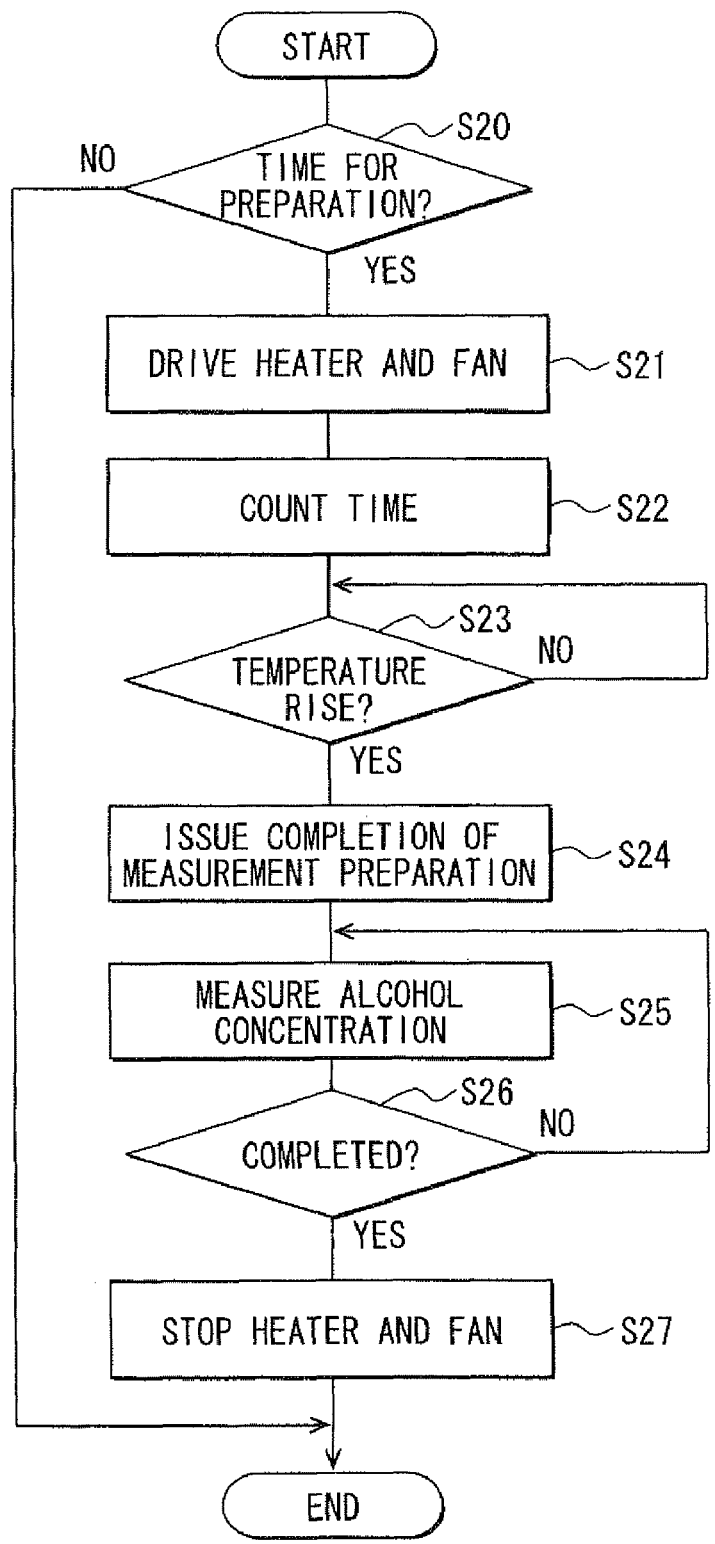
FIG. 7 is a flowchart of alcohol measurement preparation processing.

The alcohol detection ECU 10 performs alcohol measurement preparation processing shown in FIG. 7.

The ECU 10 first checks at S20 whether it is the time to perform the measurement preparation processing. If it is the time to start the measurement preparation processing, the ECU 10 resets a stable operation flag stored in its predetermined storage part and indicating that the alcohol detection device 100 is in the stable operation state, and performs S21. If it is not the time to start the measurement preparation processing, the ECU 10 ends this measurement preparation processing.

The time to start the measurement preparation processing is determined to be either a first time or a second time. The first time corresponds to a time point, at which it is detected that the driver of the vehicle having the alcohol detection system 1 approaches the vehicle and performs remote control in contactless manner for entry into the vehicle. The second time corresponds to a time point, at which certain processing is performed in the system 1 based on the detection of the remote control for entry into the vehicle. That is, the measurement preparation processing is started, when a pre-driving signal such as a remote control signal for entry into the vehicle is detected in a pre-driving period, which is before turning on an ignition switch (IG) after getting into the vehicle.

Here, the remote control operation includes entering of a driver carrying an authorized portable key 30 into a predetermined key search area around the vehicle, or a predetermined door unlock instruction operation of the driver on the portable key 30. In the processing shown in FIGS. 11 and 12 and performed by the smart entry system 20, the ECU 10 starts the measurement preparation processing when the door unlocking is permitted or instructed based on a check operation on an ID code received from the portable key 30. More specifically, when the code check ECU 300 detects an output signal (unlock permission signal) indicating permission of unlocking the door, it transmits a control signal to the alcohol detection ECU 10. The ECU 10 thus determines that it is the time to perform the measurement preparation processing. For this reason, the measurement preparation processing is started before the driver actually gets in the compartment.

At S21, the ECU 10 outputs drive instructions to drive the measurement preparation part, that is, the heater 15C and the fan 15F. The electric power of the vehicle battery VB is supplied to the heater 15C and the fan 15F to heat the alcohol sensor 11 and exhaust the gas in the chamber 19b.

At S22, the ECU 10 starts counting time by its internal timer. At S23, the ECU 10 checks whether the counted time attains a predetermined time. Since the temperature of the heater 15C driven at S21 rises as the time passes, the predetermined time corresponds to a predetermined temperature of the heater 15C. With the temperature rise, it is determined that the aging processing of the metal oxide 11B is completed and the exhausting the residual gas in the measurement chamber 19b is completed. Thus, the preparation for the next measurement of the alcohol concentration in the breath air is completed.

If the residual gas sensor 12 is provided, it is determined that the exhausting the residual gas in the measurement chamber 19b is completed when the detection result of the residual gas sensor 12 indicates a predetermined distribution of concentration of gases. In a case that the residual gas sensor 12 is the oxygen sensor, it is preferably determined that the exhausting the residual gas in the measurement chamber 19b is completed and the measurement chamber 19b is prepared for the next measurement, when the detected oxygen concentration is lower than a predetermined level. The residual gas sensor 12 is provided with a heater 15B, which is driven with the vehicle battery through the power circuit 15D to generate heat. If the ECU 10 determines at S23 that the counted time reaches the predetermined time, the residual gas sensor 12 is considered to have been heated to a predetermined temperature to operate properly as the alcohol sensor 11 is.

The ECU 10 issues a notification of completion of the measurement preparation in the vehicle compartment at S24. This notice means that the alcohol detection device 100 is changed from its initial unstable operation state to the predetermined stable operation state. This notification may be performed visually on the display unit 14 or audibly by a buzzer sound or voice sound. At this moment, the stable operation flag provided in the storage part of the ECU 10 is set.

Figure 6:
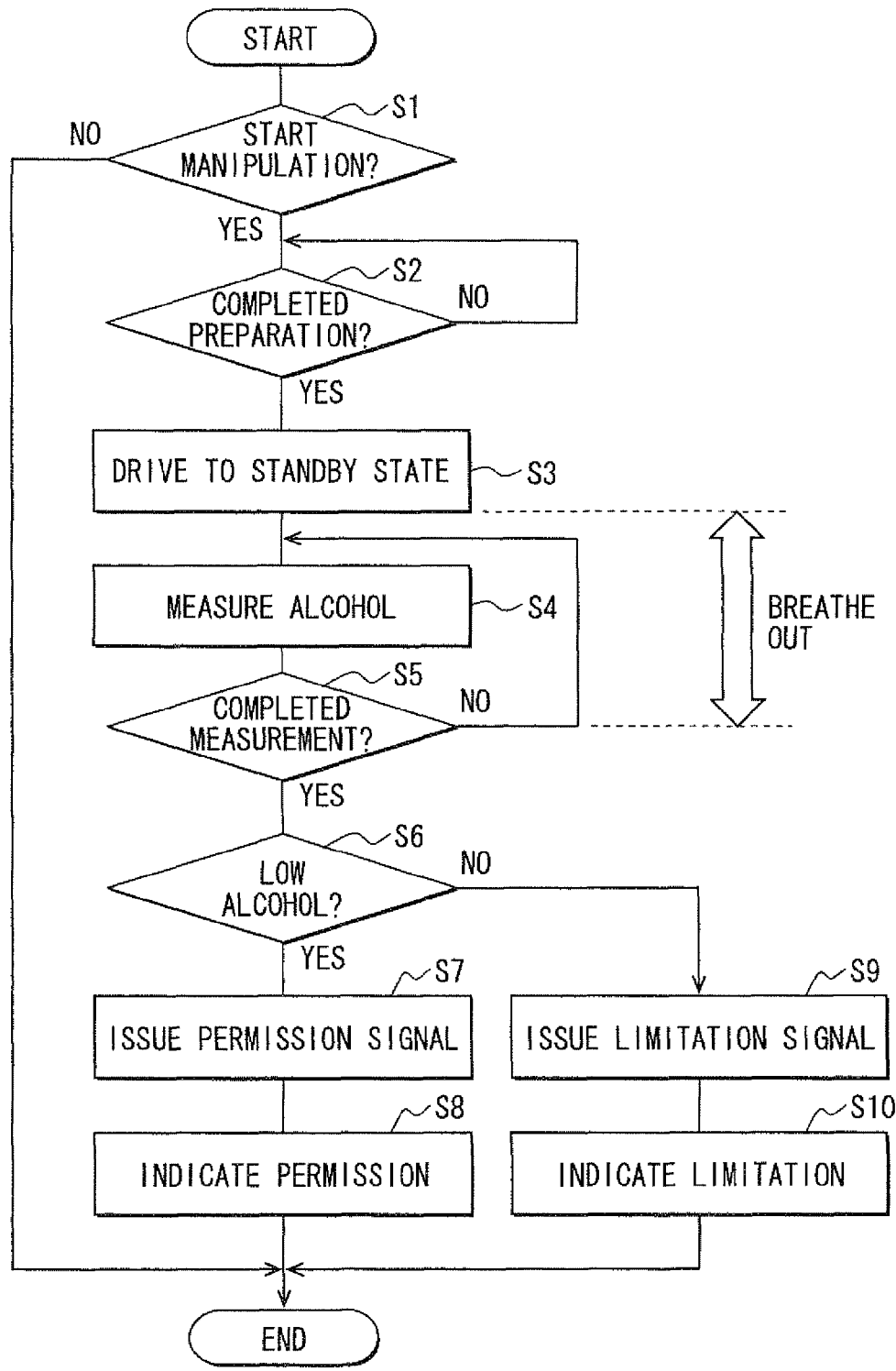
FIG. 6 is a flowchart of alcohol concentration measurement processing.

The ECU 10 starts the alcohol concentration measurement at S25, which is shown in detail in FIG. 6. The completion of alcohol concentration measurement is determined at 55 (YES) in FIG. 6. If the alcohol concentration measurement is completed, the measurement preparation part 15 (15A to 15F) is stopped from operating by shutting off the power supply from the battery VB.

The alcohol sensor 11 is configured to measure the alcohol concentration while being continuously heated by the heater 15C. It is of course possible to measure the alcohol concentration by the alcohol sensor 11 without continuously being heated, so that the power of the battery VB is saved. In this instance, the electric power supply from the battery VB to the heater 15C may be shut off at 524 when the measurement preparation operation has been completed.

Thus, the alcohol detection ECU 10 operates to detect a pre-driving output signal and instruct start of an alcohol measurement preparation operation.

The alcohol concentration measurement processing (S25 in FIG. 7) is shown in detail in FIG. 6.

The ECU 10 checks at S1 whether the alcohol concentration measurement should be started based on a predetermined manipulation for starting the measurement. This predetermined manipulation is determined to be manipulation of an ignition switch (IG) of an engine switch 40 by a driver to turn on an ignition relay. Engine start manipulation for turning on a starter switch of the engine switch 40 to turn on a starter relay is performed on an assumption that the ignition switch has been turned on. For this reason, the engine start manipulation is also the predetermined manipulation. The starter relay is not necessarily turned on at this moment. If the predetermined manipulation has been performed, the ECU 10 performs 52. If no predetermined manipulation has been performed, the ECU 10 ends this alcohol concentration measurement processing.

The ECU 10 checks at 52 whether the measurement preparation processing has been completed. Since this alcohol measurement preparation processing has already been started before the driver actually enters the vehicle, the measurement preparation processing has already been completed in some cases before the driver enters the vehicle and manipulates the engine switch 40. Even if the measurement preparation processing has not been completed, the time required for the driver to wait for the completion of the preparation processing is shortened. The ECU 10 checks whether the measurement preparation processing has been completed with reference to the state of the stable operation flag stored in its memory section. The ECU 10 repeats S2 until the measurement preparation processing is completed.

The ECU 10 drives the alcohol sensor 11 and the like of the alcohol detection device 100 to a standby state (wait state for alcohol detection) at 53. Here, the ECU 10 drives the display unit 14 to indicate visually "PLEASE BREATHE OUT." This guidance may be made audibly. The driver breathes out or blows a breath to the inlet 19a by opening a cover member of the like, which normally closes the inlet 19a. It is preferred that the measurement chamber 19b is filed with tow or more breath air of the driver. This breath air is indicated by P in FIG. 3. As a result, the oxygen concentration in the measurement chamber 19b gradually decreases and the carbon dioxide concentration in the measurement gradually increases. If the breath air of the driver breathed out or blown into the measurement chamber 19b contains alcohol, the alcohol concentration in the measurement chamber 19b gradually increases. At S4, the ECU 10 measures the alcohol concentration in the measurement chamber 19b based on the output signal of the alcohol sensor 11.

If the breath air blown into the measurement chamber 19b contacts the alcohol sensor 11, the alcohol sensor 11 changes its output signal in correspondence to the concentration of alcohol. The display unit 14 is driven to visually indicate "UNDER MEASUREMENT."

The ECU 10 checks at S5 whether the measurement of the alcohol concentration has been completed. If completed, the ECU 10 checks at S6 whether the alcohol concentration is equal to or less than a predetermined threshold level (low alcohol condition). If the alcohol concentration is low, the ECU 10 issues at 57 a control signal (permission signal) indicating travel permission to the engine ECU 500. If the alcohol concentration is high, the ECU 10 issues at S9 a control signal (limitation signal) indicating travel limitation to the engine ECU 500. The travel limitation may be a limitation on a travel speed not to exceed a predetermined low speed.

It is also possible to prohibit the engine starting operation, as the travel limitation, irrespective of the manipulation of the engine switch 40. That is, the starter relay is prohibited from being turned on. Specifically, the alcohol detection ECU 10 transmits the control signal indicating the travel limitation to the engine ECU 500, so that the engine ECU 500 does not turn on the starter relay even if the engine switch 40 is manipulated for starting the engine.

The ECU 10 drives the display unit 14 to indicate the result of measurement of the alcohol concentration, for example, as "ALCOHOL CONCENTRATION: X.XX MG/L (milligram per liter)." The display unit 14 further indicates "TRAVEL: PERMITTED" at S8 following S7, if the alcohol concentration is low. The display unit 14 however indicates "TRAVEL: LIMITED BECAUSE OF ALCOHOL" at S10 following S9, if the alcohol concentration is high. Thus, the driver is enabled to recognize the degree of the influence of alcohol drinking and limitation on vehicle travel.

The smart entry system 20 is described next.

The smart entry system 20 includes the code check ECU 300, the portable key (smart key: radio key or electronic key) 20 and the door ECU 200 as shown in FIG. 1.

More specifically, the code check ECU 300 is mounted on the vehicle and connected to an external memory unit 301, an outside radio transmitter 311, an inside radio transmitter 312, a radio receiver 320, a driver-side door unlock manipulation unit 302, a passenger-side door unlock manipulation unit 303 and the engine 40. The external memory unit 301 stores a master code (ID) specific to each vehicle. The code check ECU 300 stores in its ROM various programs to realize a smart entry system and a keyless entry system.

The outside transmitter 311 is provided at each door of a driver seat, a passenger seat and a rear luggage trunk. The outside transmitter 311 is provided in each door handle unit and regularly transmits an inquiry signal (polling signal or request signal: long wavelength (LF) band electromagnetic wave) in an outward direction around the vehicle. This inquiry signal is adjusted to reach only a predetermined distance (0.7 to 1.0 m) from each door thereby to form a key response area (outside detection area).

The inside transmitter 312 is provided inside the vehicle and is provided at one of or both of a front part and a rear part of a vehicle compartment. The inside transmitter 312 is also provided in a rear luggage trunk. The inside transmitter 312 regularly transmits an inquiry signal (long wavelength (LF) band electromagnetic wave) into the vehicle compartment. This inquiry signal is adjusted to reach only a predetermined key response area in the compartment.

The receiver 320 receives a response signal of the portable key 30 in each key response area or a manipulation signal (lock/unlock request signal: radio frequency (high frequency) band electromagnetic wave), and sends a received response signal to the code check ECU 300. The inquiry signal transmitted from the portable key 30 includes data, which is used to determine in which one of the areas the portable key 30 is.

The portable key 30 includes a radio receiver 31 for receiving electromagnetic wave of the long wavelength (LF) band, a radio transmitter 32 for transmitting electromagnetic wave of the radio frequency (RF) band, a door unlock manipulation switch 33, a door lock manipulation switch 34, and a control unit 35. The control unit 35 stores an ID code specific to a vehicle for which the portable key 30 is authorized. When the inquiry signal (polling signal) from the transmitter 311 or 312 is received by the receiver 31 or when the manipulation switch 33 or 34 is operated, the control unit 35 is activated and drives the transmitter 32 to transmit the response signal so that the response signal is received by the receiver 320 of the code check ECU 300. This response signal includes the ID code assigned to the portable key 30 and stored in its memory.

The door ECU 200 is provided to control lock or unlock of each door of the vehicle. The door ECU 200 is connected to a door lock drive units (motors and drive circuits) 201, 202, door lock state detection units 211, 212 and door open/close detection units 221, 222. The door lock drive units 201 and 202 switch over the lock/unlock state of each door lock mechanism of the driver-side door and the passenger-side doors, respectively. The door open/close detection units 221 and 222 detect the door lock states by checking whether the driver-side door and the passenger-side doors are locked or unlocked, respectively. The door open/close detection units 221 and 222 detect the door open/close states by checking whether the driver-side door and the passenger-side doors are opened or closed, respectively.

Figure 11:
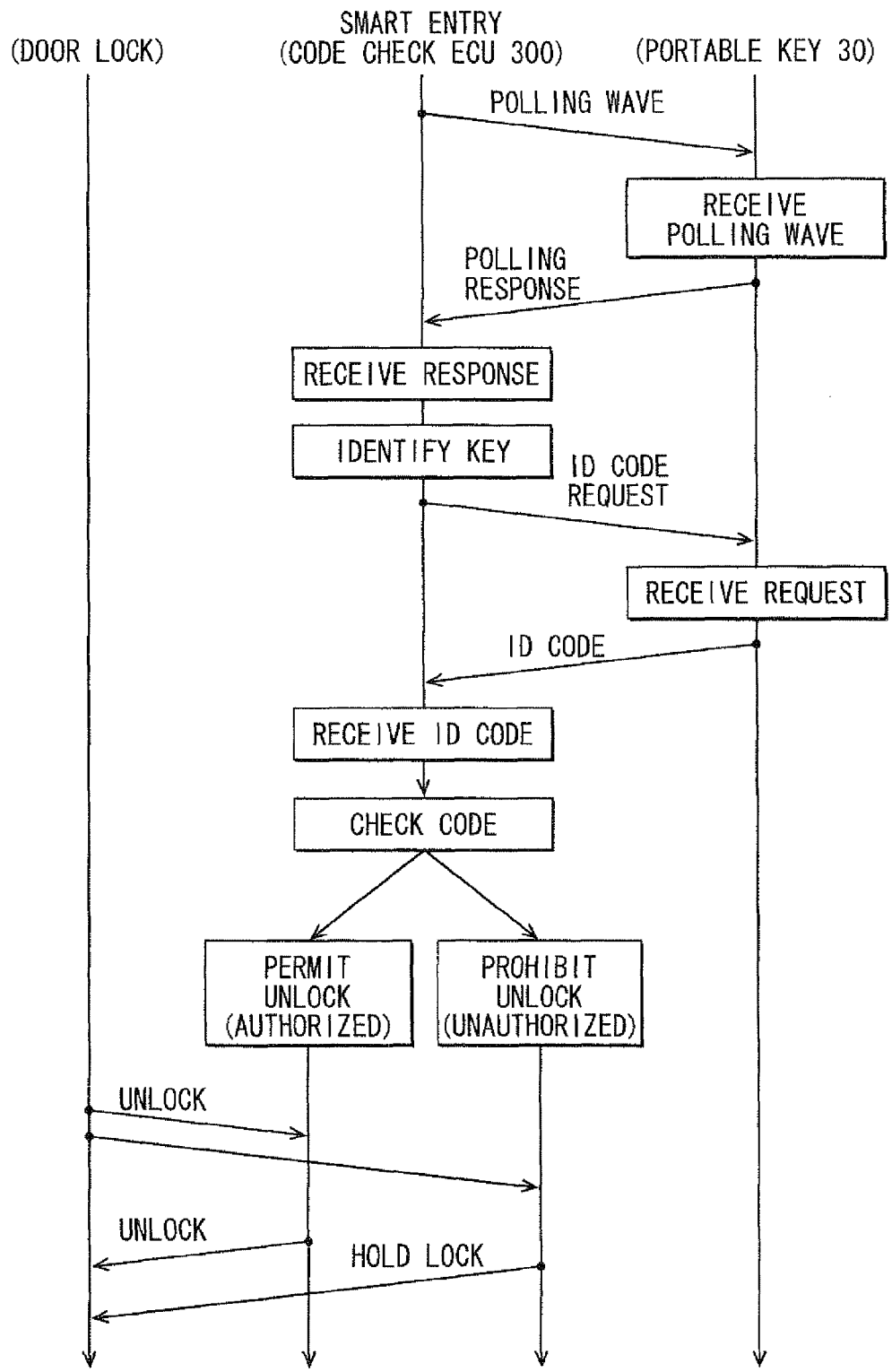
FIG. 11 is a flowchart of door unlocking processing performed in a smart entry operation.

Door unlocking processing in the smart entry system is shown in FIG. 11. The code check ECU 300 regularly drives the outside transmitter 311 to transmit the polling signal (polling wave) as the inquiry signal for searching for the portable key 30 outside the vehicle. When the driver carrying the portable key 30 enters the key response area (outside detection area) defined by the polling signal, the portable key 30 receives the polling signal by its receiver 31 and transmits the response signal from the transmitter 32. When the receiver 320 in the vehicle receives the response signal, the code check ECU 300 performs whether the portable key 30, which corresponds to the subject vehicle, is present. If the presence is confirmed, the code check ECU 300 drives the transmitter 311 to transmit the request signal for requesting the ID code. The portable key 30, receiving the request signal by the receiver 31, transmits the response signal including the ID code stored in the control unit 35 from the transmitter 32. When the code check ECU 300 receives the response signal including the ID code, it checks whether this received ID code corresponds to the master code stored in the code check ECU 300. If the codes match, that is, the portable key 30 is the authorized one, the code check ECU 300 outputs a control signal to the door ECU 200 for permitting the unlocking of the doors by the door ECU 200. If the codes do not match, that is, the portable key 30 is not the authorized one, the code check ECU 300 outputs a control signal to the door ECU for prohibiting the unlocking of the doors by the door ECU 200.

If the driver performs the door unlocking operation on the door unlocking manipulation unit 302 or 303 under the condition that the unlocking of the door lock mechanism is permitted by the control signal as described in FIG. 11, that is, unlock permission mode, the door on which the unlocking manipulation is performed is unlocked by the door lock driver unit 201 and/or 202. If the driver performs the door unlocking operation on the door unlocking manipulation unit 302 or 303 under the condition that the unlocking of the door lock mechanism is prohibited by the control signal as described in FIG. 11, that is, in the unlock prohibition mode, the door on which the unlocking manipulation is performed is held locked by the door lock driver units 201 and 202 and not unlocked.

The foregoing embodiment may be modified in many ways. Some of such modifications will be described below.

The start time for the measurement preparation processing may be set to any other time, as far as it is before the alcohol concentration measurement start manipulation (for example, engine switch manipulation for turning on the ignition). It is preferably before the door is opened from the outside by the driver, and more preferably before the door is unlocked by the driver. By starting the measurement preparation processing at the earlier time, the alcohol concentration measurement can be started at the earlier time correspondingly so that the driver is permitted to start the engine operation and drive the vehicle at the earlier time. The alcohol detection ECU 10 may output the control signal for instructing the start of the measurement preparation processing upon receiving from any other ECUs a signal indicating that the driver will soon use the vehicle.

The start time of the measurement preparation processing may be set to time, at which a predetermined output signal is received from the portable key 30 in the door unlock processing of the smart entry system. In this instance, the code check ECU 300 outputs a control signal to instruct a start of measurement preparation processing to the alcohol detection ECU 10 when the code check ECU 300 detects a predetermined output signal generated in the vehicle in response to the predetermined output signal transmitted from the portable key 30. By starting the measurement preparation processing irrespective of the contents (for example, ID code) included in the received signal, the processing is simplified and started quickly.

Further, the start time of the measurement preparation processing may be set to another time, at which the predetermined door unlock manipulation performed on the manipulation unit 302 or 303 is detected by the code check ECU 300 under the condition that the ID code of the portable key 30 is confirmed as matching the master code and the door unlock permission signal is outputted to the door ECU 200. The code check ECU 300 outputs the control signal to the alcohol detection ECU 10 to start the measurement preparation processing.

The signal for instructing the start of alcohol measurement preparation processing may be a predetermined signal, which is issued without fail in connection with the door unlocking operation in a keyless entry system different from the smart entry system.

Figure 12:
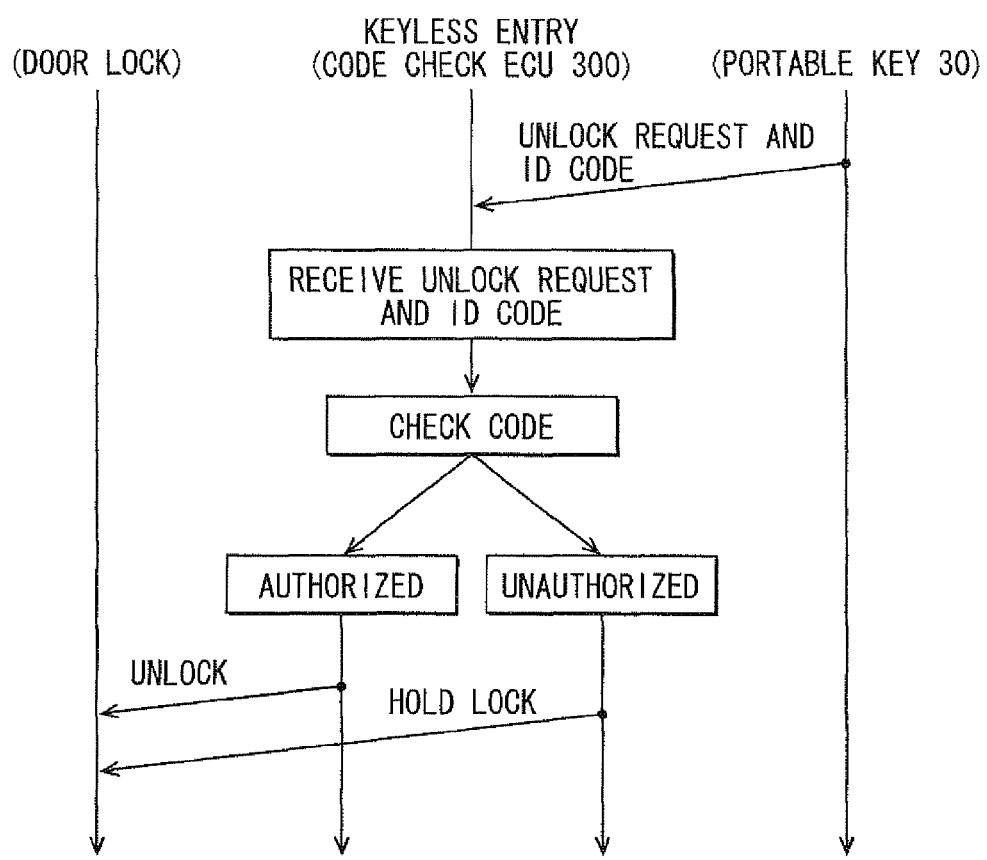
FIG. 12 is a flowchart of door unlocking processing performed in a keyless entry operation.

The smart entry system 20 may also include the keyless entry system to instruct lock and/or unlock of the doors by manipulating the door unlock switch 33 and the door lock switch 34 of the portable key 30. The door unlock processing is performed by the keyless entry system 20 as shown in FIG. 12. The portable key 30 is provided with the door unlock switch 33 as shown in FIG. 8. When the driver manipulates the door unlock switch 33, the control unit 35 is activated to drive the transmitter 32 to transmit a signal, which includes a door unlock request and the ID code stored in the control unit 35. When the receiver 320 in the vehicle receives this signal, the code check ECU 300 compares the received ID code with its master code. If both codes match or agree indicating that the portable key 30 is the authorized one, the ECU 300 issues the control signal to the door ECU 200 for instructing the unlocking of doors If both codes do not match, the ECU 300 do not issue the control signal so that the door ECU 200 does not unlock doors.

When the door ECU 200 receives the control signal, which instructs the unlocking of corresponding doors, the driver-side door and/or the passenger-side door are unlocked by the door unlock drive units 302 and 303, respectively. When the door ECU 200 does not receive the control signal, the doors are held locked.

If the keyless entry system is mounted in the vehicle, the measurement preparation processing may be started when the unlocking of door is determined based on both the result of checking the ID code received from the portable key 30 under the smart entry system and the door unlock request received from the portable key 30 under the keyless entry system. Specifically, the code check ECU 300 first detects the predetermined signal (pre-driving output signal), which is outputted at the time of unlocking the door based on the code check result and the door unlock request, and then issues the control signal to the alcohol detection ECU 10 to thereby instruct the measurement preparation processing. It is also possible to output the control signal for instructing the start of alcohol measurement preparation processing from the code check ECU 300 to the alcohol detection ECU 10, when the code check ECU 300 receives a certain signal from the portable key 30.

If the door unlock processing is possible in any of the smart entry system and the keyless entry system, the start time of the measurement preparation processing is preferably set in each of the entry systems. If the door unlock processing is possible under only the keyless entry system, the start time of the measurement preparation processing should be set in connection with the door unlock processing of the keyless entry system.

The smart entry system and the keyless entry system may accidentally become inoperative. For such an instance, the start time of alcohol measurement preparation processing may be set irrespective of the smart entry system and the keyless entry system. For example, the control signal for instructing the start of alcohol measurement preparation processing may be issued to the alcohol detection ECU 10, when the door ECU 200 detects change of the door (door lock mechanism) is unlocked from the locked state based on the detection result of the door lock state detection unit 211 or 212. If the measurement preparation processing has already been started, the same processing need not be started at this moment.

The control signal for instructing the start of alcohol measurement preparation processing may alternatively be issued to the alcohol detection ECU 10, when the door ECU 200 detects based on the detection result of the door open/close state detection unit 221 or 222 that the door is opened from the closed state. This setting of the start time of alcohol measurement preparation processing may be performed in vehicles, which are not equipped with any of the smart entry system and the keyless entry system.

It is also possible to start the measurement preparation processing when the result of code check processing performed in the door unlock processing in the smart entry system or the keyless entry system indicates the agreement or matching of the ID code with the master code, that is, the portable key is the authorized one.

In many instances, a vehicle having the smart entry system 20 has also a smart start system. In the embodiment shown in FIG. 1, a smart start system 50 is formed by the portable key 30, the code check ECU 300, the engine switch 40 and the engine ECU 500. The smart start system may be formed such that, when the driver carrying the portable key 30 enters an in-vehicle key search area (in-vehicle detection area) in the vehicle compartment, the code check ECU 300 detects an output signal indicating a reception of a predetermined signal transmitted from the portable key 30 or a predetermined output signal (pre-driving output signal) issued in predetermined processing of the smart start system performed in response to the predetermined signal of the portable key 30.

Figure 13:
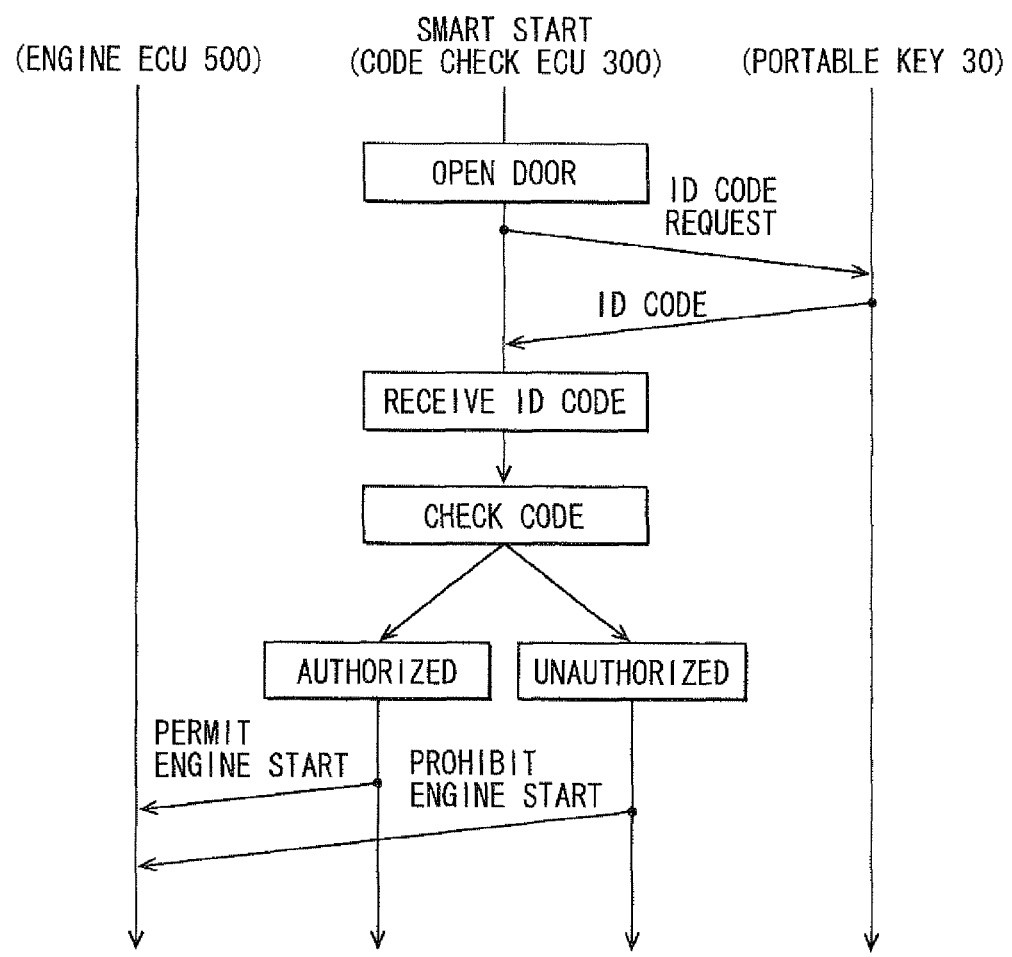
FIG. 13 is a flowchart of engine starting processing performed in a smart start operation.

Engine start processing performed by the smart start system 50 is shown in FIG. 13.

In this processing, when the door is opened, the code check ECU 300 transmits an ID code request signal in the compartment from the inside transmitter 312 and receives a response signal from the portable key 30 through the receiver 320. If the ID code included in the received response signal matches the master code, that is, if the portable key 30 is the authorized one, the code check ECU 300 issues a control signal to the engine ECU 500 for permitting the starting of engine. If the codes do not match, that is, if the portable key 30 is not the authorized one, the code check ECU 300 issues a control signal to the engine ECU 500 for prohibiting the starting of engine.

In this configuration, the alcohol detection ECU 10 may start the measurement preparation processing, when the code check ECU 300 detects the response signal including the ID code and sends a response detection signal to the alcohol detection ECU 10. Alternatively, the alcohol detection ECU 10 may start the measurement preparation processing, when the code check ECU 300 confirms matching of codes and issues a control signal to the alcohol detection ECU 10 thereby instructing the start of the measurement preparation processing.

Various communications performed in the door unlock processing in the smart entry system and the keyless entry system and performed between the portable key and the vehicle in the engine start processing in the smart start system is not limited to radio communications processing. The communications may include more or less communications processing. For example, it is possible to add communications, in which the transmitter 311 or 312 transmits a challenge signal after receiving the ID code from the portable key 30, the portable key 30 returns it by performing predetermined coding, and the code check ECU 300 decodes the returned challenge signal. Thus, without limiting the start time of the measurement preparation processing to the time, at which the code matching is confirmed, the start time of the measurement preparation processing may be set at the time, at which the unlocking of doors is finally permitted. This will reduce power consumption.

Figure 14:
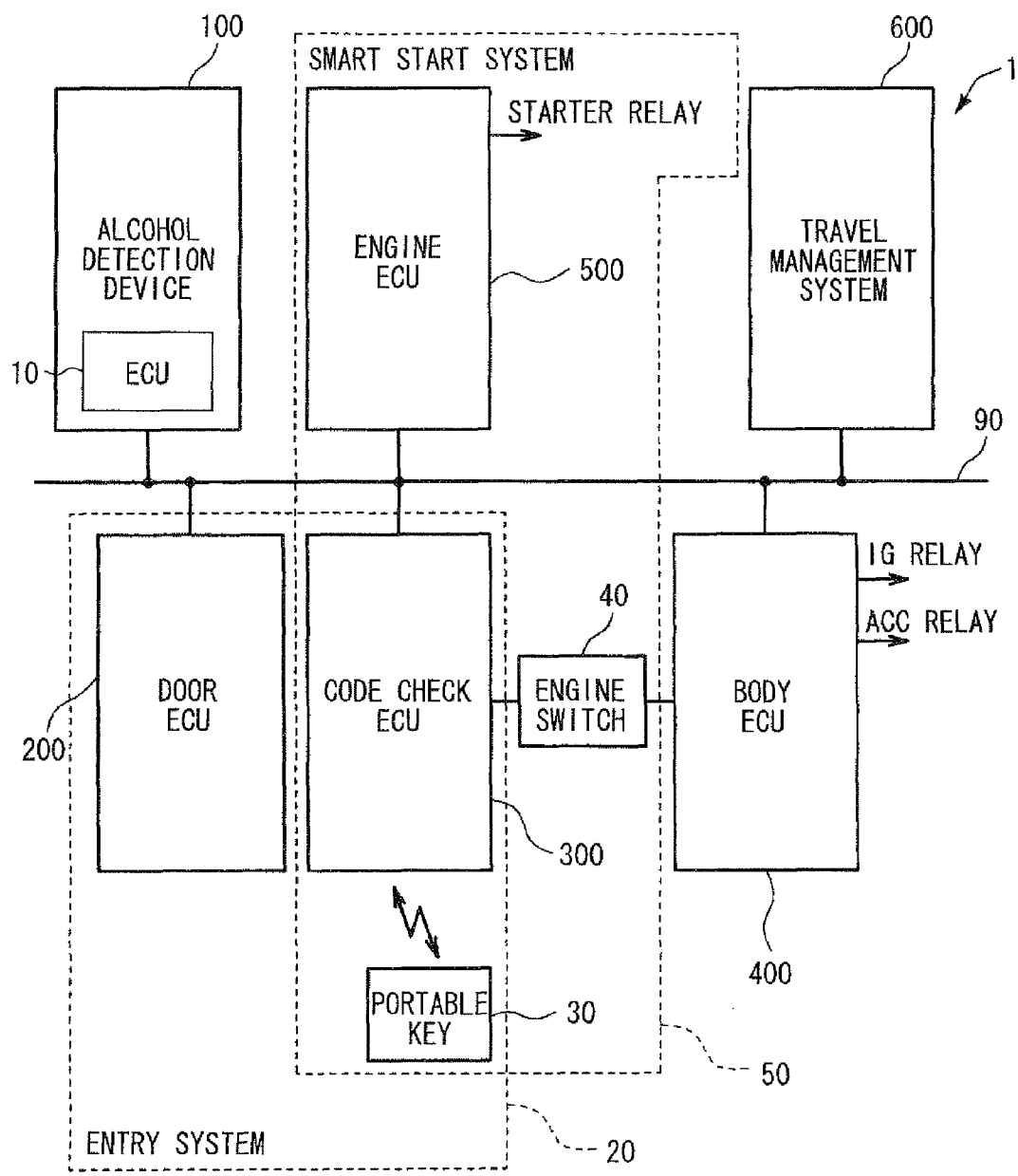
FIG. 14 is a block diagram of an alcohol detection system according to modification of the embodiment.
Figure 15:
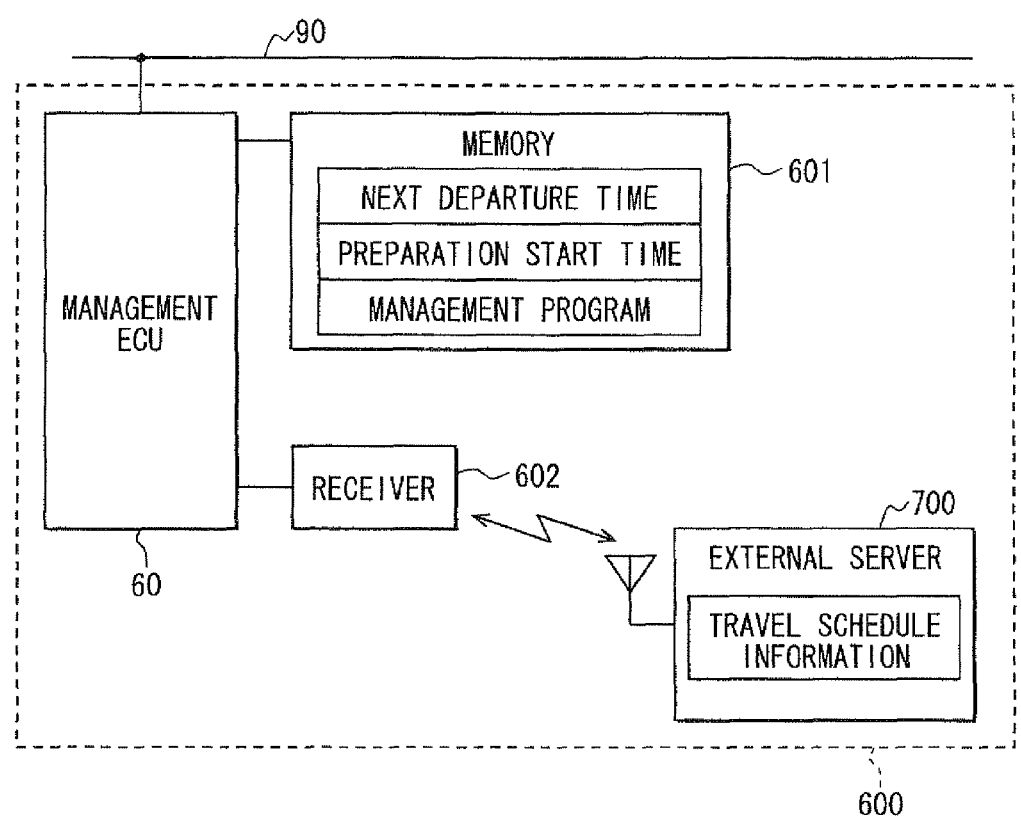
FIG. 15 is a block diagram of an example of a travel management system shown in FIG. 14.

The measurement preparation processing may be implemented as shown in FIGS. 14 and 15, in which a travel management system 600 is provided.

The travel management system 600 includes an external server 700, which stores travel schedule information of each vehicle, for managing departure time of a number of vehicles. Each vehicle is equipped with a travel management ECU 60, which is also a microcomputer including a CPU, a clock IC and the like. The clock IC provides or set time and calendar data upon request from the CPU, so that the ECU 60 may acquire information about date and hour (time). The ECU 60 performs a travel management program stored in a memory 601. Specifically, the ECU 60 receives next departure time information transmitted from the external server 700 through a receiver 602 and stores it in the memory 601. Based on the stored next departure time information of the memory 601 and the date and hour information acquired from the clock IC, the ECU 601 detects a relevant time point, which is a predetermined time (for example, five minutes) before the next departure time. The ECU 60 then issues a control signal to the alcohol detection ECU 10 for instructing the start of alcohol measurement preparation processing. As a result, the driver can be subjected to the checking of alcohol drinking immediately or soon after getting in the vehicle and before the scheduled departure time.

The travel management system 600 may be configured to include a reference time setting part, a reference time output part and a reference time signal detection unit so that all the necessary processing may be made within the vehicle without external devices. The reference time setting part sets predetermined reference time (for example, departure time, scheduled departure time). The reference time output part outputs a reference time signal when predetermined time of the measurement preparation time arrives. This alcohol measurement preparation time is set to be earlier than the set reference time. The reference time signal detection part detects the outputted reference time signal. For example, an input manipulation part is provided for inputting the scheduled departure time and the start time of alcohol measurement preparation processing in advance of the scheduled departure time.

The alcohol detection device 100 may be any type, which requires alcohol measurement preparation processing to attain a predetermined fixed operation state from an initial state. For example, the alcohol sensor 11 may be a type, which uses a change in the electromotive force produced by electrochemical reaction. It may also be a type, which uses a characteristic that molecule of alcohol vapor absorbs an infra-red ray of a specified wavelength. The measurement preparation processing may include not only the heating operation of the heater 15C but also the exhausting of the residual gas in the measurement chamber 19b. It is noted that the heating operation as the measurement preparation processing is particularly of advantage in case the alcohol sensor 11 is configured as a semiconductor-type sensor.

The travel limitation according to the alcohol detection result is not limited to disabling of the engine starting operation but may be limiting the travel speed of the vehicle to a sufficiently low speed. For example, the engine ECU 500 may be configured such that the engine is controlled to suppress the vehicle speed detected by a vehicle travel speed sensor 401 (FIG. 10) to be lower than a predetermined speed. Alternatively, the shift position may be prohibited from being changed to the drive position.

The fan 15F may be controlled to operate in different modes, an exhaust mode and an agitation mode. In the exhaust mode, the fan 15F exhausts the residual gas in the measurement chamber 19b into outside of the casing 19. In the agitation mode, the fan 15F agitates the introduced breath air within the measurement chamber 19b. The fan 15F is driven to rotate at lower speeds in the agitation mode than in the exhaust mode.

The heater 15C may be operated periodically at a predetermined interval while the vehicle is at rest, so that the time required to attain the temperature rise (523 in FIG. 7) in the measurement preparation processing may be shortened.

What is claimed is:

1. An alcohol detection system for a vehicle comprising:
    an alcohol detection section that detects alcohol concentration in breath air of a user seating in a driver's seat in a vehicle, the alcohol detection section including a measurement chamber for receiving the breath air of the user to be measured and a fan for exhausting residual gas in the measurement chamber;
    a measurement preparation operation section that performs at least driving operation of the fan, as an alcohol measurement preparation operation, which changes the alcohol detection section from an initial state to a predetermined stable operation state;
    a travel control section that permits normal travel of the vehicle when alcohol concentration measured under the predetermined stable operation state is below a predetermined threshold level, and prohibits travel of the vehicle over a predetermined travel speed when the alcohol concentration is over the threshold level;
    a pre-driving output signal detection section that detects a predetermined pre-driving output signal outputted necessarily before an ignition switch is manipulated by the user entering the vehicle from an outside of the vehicle; and
    a measurement preparation operation start instruction section that instructs the measurement preparation operation section to start the measurement preparation operation when the pre-driving output signal is detected.

2. The alcohol detection system according to claim 1, wherein:
    the alcohol detection section changes to the stable operation state by being heated to a predetermined temperature at a predetermined sensor part; and
    the measurement preparation operation section performs a heating operation as the measurement preparation operation.

3. The alcohol detection system according to claim 1, wherein:
the per-driving output signal is generated when the user is outside the vehicle and before entering the vehicle.

4. The alcohol detection system according to claim 1, wherein:
the pre-driving output signal detection section detects, as the pre-driving output signal, a predetermined output signal generated when the user performs a predetermined pre-driving operation required in a pre-driving period.

5. The alcohol detection system according to claim 4, wherein:
the pre-driving output signal detection section is operatively coupled with a smart entry system of the vehicle, which transmits a polling wave in a predetermined key search area around the vehicle, checks an ID code received from a smart key in response to the polling wave, permits unlocking of a door based on a check result of the ID code, and unlocks the door in response to detection of a predetermined door unlock operation of the driver; and
the pre-driving output signal detection section defines, as the pre-driving operation, an area entering operation, in which the user carrying the smart key enters in the predetermined key search area, and detects, as the pre-driving output signal, a predetermined output signal generated in the smart entry system in response to reception of a radio signal transmitted from the smart key or a predetermined output signal generated in a course of operation performed in the smart entry system following the reception of a radio signal.

6. The alcohol detection system according to claim 5, wherein:
the pre-driving output signal detection section detects, as the pre-driving output signal, a predetermined output signal generated in the smart entry system to indicate permission of the unlocking of a door as a result of checking of the ID code.

7. The alcohol detection system according to claim 5, wherein:
the pre-driving output signal detection section detects, as the pre-driving output signal, a predetermined output signal generated in the smart entry system in response to the detection of a predetermined door unlock operation under a condition that the check result of the ID code indicates that the unlocking of a door is permitted.

8. The alcohol detection system according to claim 4, wherein:
the pre-driving output signal detection section is operatively coupled with a keyless entry system of the vehicle, which receives a door unlock request signal and an ID code from a portable key of the driver, checks the ID code, and unlocks a door based on a check result of the ID code and the door unlock request signal; and
the pre-driving output signal detection section defines, as the pre-driving operation, a predetermined door unlock operation made on the portable key carried by the user, and detects, as the pre-driving output signal, an output signal generated in the keyless entry system in response to reception of a radio signal transmitted from the portable key or an output signal generated in a course of operation performed in the keyless entry system following the reception of a radio signal.

9. The alcohol detection system according to claim 8, wherein:
the pre-driving output signal detection section detects, as the pre-driving output signal, a predetermined output signal generated in the keyless entry system to unlock the door based on the check result of the ID code and the door unlock request signal.

10. The alcohol detection system according to claim 4, wherein:
the pre-driving output signal detection section defines, as the pre-driving operation, a door unlock operation by the user outside the vehicle, and detects, as the pre-driving output signal, a predetermined output signal generated when a door of the vehicle is unlocked in response to a predetermined door unlocking manipulation of the driver performed before entering the vehicle.

11. The alcohol detection system according to claim 4, wherein:
the pre-driving output signal detection section defines, as the pre-driving operation, a door opening operation by the user outside the vehicle, and detects, as the pre-driving output signal, a predetermined output signal generated when a door of the vehicle is opened from a closed state before entering the vehicle.

12. The alcohol detection system according to claim 1, wherein:
the pre-driving output signal detection section detects, the measurement preparation operation start instruction means detects, as the pre-driving output signal, a reference time signal generated at a predetermined measurement preparation start time, which is set to be earlier than a predetermined reference time.

13. The alcohol detection system according to claim 1, wherein:
the measurement preparation start instruction section outputs a drive instruction for starting the measurement preparation operation in response to detection of the pre-driving output signal outputted from a device mounted in the vehicle; and
the measurement preparation start instruction section drives an operation part for performing the measurement preparation operation when the drive instruction is outputted, by power supply from a battery mounted in the vehicle.

14. The alcohol detection system according to claim 2, wherein:
the per-driving output signal is generated when the user is outside the vehicle and before entering the vehicle.

15. The alcohol detection system according to claim 2, wherein:
the pre-driving output signal detection section detects, as the pre-driving output signal, a predetermined output signal generated when the user performs a predetermined pre-driving operation required in a pre-driving period.

16. The alcohol detection system according to claim 2, wherein:
the pre-driving output signal detection section detects, the measurement preparation operation start instruction means detects, as the pre-driving output signal, a reference time signal generated at a predetermined measurement preparation start time, which is set to be earlier than a predetermined reference time.

17. The alcohol detection system according to claim 2, wherein:
the measurement preparation start instruction section outputs a drive instruction for starting the measurement preparation operation in response to detection of the pre-driving output signal outputted from a device mounted in the vehicle; and the measurement preparation start instruction section drives an operation part for performing the measurement preparation operation when the drive instruction is outputted, by power supply from a battery mounted in the vehicle.

18. The alcohol detection system according to claim 3, wherein:

the pre-driving output signal detection section detects, as the pre-driving output signal, a predetermined output signal generated when the user performs a predetermined pre-driving operation required in a pre-driving period.

19. The alcohol detection system according to claim 3, wherein:

the measurement preparation start instruction section outputs a drive instruction for starting the measurement preparation operation in response to detection of the pre-driving output signal outputted from a device mounted in the vehicle; and the measurement preparation start instruction section drives an operation part for performing the measurement preparation operation when the drive instruction is outputted, by power supply from a battery mounted in the vehicle.

20. The alcohol detection system according to claim 4, wherein:

the measurement preparation start instruction section outputs a drive instruction for starting the measurement preparation operation in response to detection of the pre-driving output signal outputted from a device mounted in the vehicle; and the measurement preparation start instruction section drives an operation part for performing the measurement preparation operation when the drive instruction is outputted, by power supply from a battery mounted in the vehicle.

* * * * *